(12) United States Patent
Just

(10) Patent No.: US 8,911,395 B2
(45) Date of Patent: Dec. 16, 2014

(54) SYRINGE CARPULE FOR STORING, TRANSPORTING AND IN SITU MIXING OF LIDOCAINE AND SODIUM BICARBONATE AND DELIVERY OF BUFFERED ANESTHETIC SOLUTION

(71) Applicant: George Just, Monroeville, PA (US)

(72) Inventor: George Just, Monroeville, PA (US)

( * ) Notice: Subject to any disclaimer, the term of this patent is extended or adjusted under 35 U.S.C. 154(b) by 113 days.

(21) Appl. No.: 13/666,275

(22) Filed: Nov. 1, 2012

(65) Prior Publication Data

US 2013/0110039 A1    May 2, 2013

Related U.S. Application Data

(60) Provisional application No. 61/554,162, filed on Nov. 1, 2011.

(51) Int. Cl.
*A61M 37/00* (2006.01)
*A61M 5/00* (2006.01)
*A61M 5/24* (2006.01)
*A61M 5/31* (2006.01)
*A61M 5/32* (2006.01)
*A61M 5/315* (2006.01)

(52) U.S. Cl.
CPC ..... *A61M 5/2448* (2013.01); *A61M 2005/2414* (2013.01); *A61M 5/2459* (2013.01); *A61M 5/3137* (2013.01); *A61M 5/2466* (2013.01); *A61M 5/3243* (2013.01); *A61M 5/31511* (2013.01)
USPC ............................. 604/87; 604/232; 604/191

(58) Field of Classification Search
USPC ................. 604/87, 88, 187, 191, 201–206, 604/232–236, 415
See application file for complete search history.

(56) References Cited

U.S. PATENT DOCUMENTS

| | | | |
|---|---|---|---|
| 2,671,450 A | | 3/1954 | Dann |
| 2,705,956 A | * | 4/1955 | McLaughlin ................ 604/404 |
| 3,848,593 A | | 11/1974 | Baldwin |
| 4,254,768 A | | 3/1981 | Ty |
| 4,333,457 A | | 6/1982 | Margulies |
| 4,490,142 A | | 12/1984 | Silvern |

(Continued)

OTHER PUBLICATIONS

Christoph R. A. Buchanan L., et al: Pain Reduction in Local Anesthetic Administration Through pH Buffering. Annal of Emerg Med 1988. 17, 117-120.

(Continued)

*Primary Examiner* — Nicholas Lucchesi
*Assistant Examiner* — Leah Stohr
(74) *Attorney, Agent, or Firm* — Blynn L. Shideler; Krisanne Shideler; BLK Law Group

(57) ABSTRACT

A syringe carpule for storing, transporting and in situ mixing of a local anesthetic, such as lidocaine, and a buffer, such as sodium bicarbonate, and delivery of buffered anesthetic solution according to the present invention that comprises a hollow tubular body received within the frame of a carpule syringe, at least one axially movable plunger within the body and configured to be engaged and moved by a rod of the carpule syringe, a seal pierced by a rear portion of a needle coupled to the carpule syringe, a first chamber within the body filled with anesthetic solution during storing and transport, a second chamber defined within the body filled with buffering solution during storing and transport; and a breachable separating member between the first and second chamber configured to be removed for in situ mixing of the buffering and the anesthetic solutions allowing for delivery of a buffered anesthetic solution.

15 Claims, 2 Drawing Sheets

(56) References Cited

U.S. PATENT DOCUMENTS

| | | | |
|---|---|---|---|
| 4,915,701 | A | 4/1990 | Halkyard |
| 4,919,657 | A | 4/1990 | Haber et al. |
| 4,931,040 | A | 6/1990 | Haber et al. |
| 5,069,670 | A | 12/1991 | Vetter et al. |
| 5,112,307 | A | 5/1992 | Haber et al. |
| 5,137,528 | A * | 8/1992 | Crose .......................... 604/415 |
| 5,269,766 | A | 12/1993 | Haber et al. |
| 5,330,440 | A | 7/1994 | Stanners et al. |
| 5,542,934 | A | 8/1996 | Silver |
| 5,788,670 | A | 8/1998 | Reinhard et al. |
| 6,349,850 | B1 | 2/2002 | Cheikh |
| 6,544,233 | B1 | 4/2003 | Fukui et al. |
| 6,645,179 | B1 | 11/2003 | Ishikawa et al. |
| 8,092,421 | B2 | 1/2012 | Seiferlein et al. |
| 2003/0036724 | A1 | 2/2003 | Vetter et al. |
| 2006/0173409 | A1 | 8/2006 | Yang |

OTHER PUBLICATIONS

Stewart J. H. Chinn S. E. et al.: Neutralized Lidocaine with Epinephrine for Local Anesthesia. J. Dermatol Surg Oncol 1990. Abstract.

Steinbrook R. A. Hughes N. et al.: Effects of Alkalinization of Lidocaine on the Pain of Skin Infiltration and Intravenous Catheterization. J. Clin Anesth, Nov. 5/Dec. 1993, 456-8 Abstract.

Armel H. E. and Horowitz M., Alkalinization of Local Anesthesia with Sodium Bicarbonate—Preferred Method of Local Anesthesia. Urology. 1994. 101 Abstract.

Suraj Achar, M.D. and Suriti Kundu, M.D., Principles of Office Anesthesia: Part I. Infiltrative Anesthesia, Am Fam Physician. Jul. 1, 2002;66(1):91-95.

Nancy Walsh, Warm Local Anesthetic Eases Injection Pain, Annals of Emergency Medicine, Feb. 10, 2011.

Larson Po, Stability of buffered lidocaine and epinephrine used for local anesthesia, Department of Surgery, Journal of dermatologic surgery and oncology, May 1991;17(5):411-4, Abstract.

Buchanan L, Christoph RA, Pain reduction in local anesthetic administration through pH buffering, Ann Emerg Med, Feb. 1988;17(2):117-20, Abstract.

Stanley F. Malamend, DDS., Buffering Local Anesthetics in Dentistry, The Pulse, vol. 44, Issue 1, 2011.

* cited by examiner

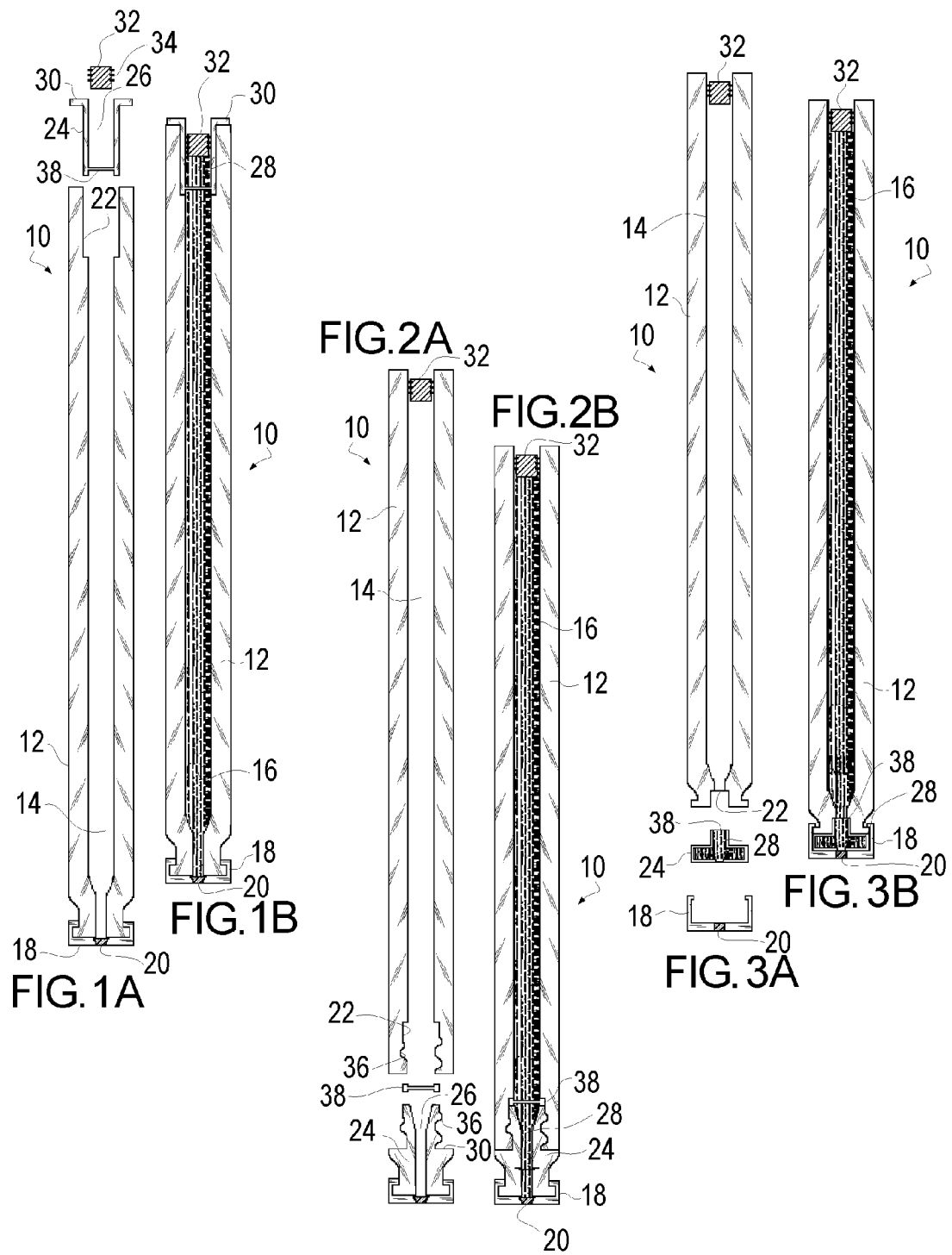

SYRINGE CARPULE FOR STORING, TRANSPORTING AND IN SITU MIXING OF LIDOCAINE AND SODIUM BICARBONATE AND DELIVERY OF BUFFERED ANESTHETIC SOLUTION

RELATED APPLICATIONS

The present application claims the benefit of Provisional Patent Application Ser. No. 61/554,162 filed on Nov. 1, 2011 and entitled "Syringe Carpule for Storing, Transporting and In Situ Mixing of Lidocaine and Sodium Bicarbonate and Delivery of Buffered Anesthetic Solution."

BACKGROUND OF THE INVENTION

1. Field of the Invention

The present invention relates to carpule syringes and more specifically associated syringe carpules for storing, transporting and in situ mixing of a local anesthetic, such as lidocaine, and a buffer, such as sodium bicarbonate, and delivery of buffered anesthetic solution.

2. Background Information

The present invention relates delivery of buffered anesthetic solution. As background, the essentially first "modern" local anesthetic agent was lidocaine (original trade name Xylocaine®). Lidocaine was first introduced in the late 1940s. Prior to its introduction, Nitrous oxide gas and procaine (plus alcohol in the form of whiskey) were the major sources of pain relief during dental procedures. Lidocaine proved to be so successful that during the late 1940s and throughout the 1950s that the use of procaine and nitrous oxide gas as primary anesthetic agents all but vanished. With some professionals humorously noting that whiskey survived, but it is no longer used on patients.

Lidocaine (along with all other injectable anesthetics used in modern dentistry) is in a broad class of chemicals called amides, and unlike ester based anesthetics, amides are hypoallergenic. Lidocaine sets quickly and may conventionally be combined with a small amount of epinephrine (adrenalin) to produce profound anesthesia for several hours. Lidocaine is still the most widely used local anesthetic in America today. Lidocaine conventionally comes in a variety of dosage forms, including injectable, topical jelly, and oral/topical viscous solution. Common strengths are 1%, 2% and 4%. The percentage of lidocaine is an indication of the total by weight percent, such that one percent lidocaine means that there is one gram of lidocaine in one hundred total milliliters of liquid solution.

In order to alleviate the pain experienced by local anesthetic injections medical professionals often add sodium bicarbonate ($NaHCO_3$) to the selected anesthetic in order to alkalize the medication. Several articles have been written on the subject matter such as follows: Christoph R. A. Buchanan L., et al.: Pain Reduction in Local Anesthetic Administration Through pH Buffering. Annal of Emerg Med 1988. 17, 117-120.; Stewart J. H. Chinn S. E. et al.: Neutralized Lidocaine with Epinephrine for Local Anesthesia. J. Dermatol Surg Oncol 1990. 16, 842-845; Steinbrook R. A. Hughes N. et al.: Effects of Alkalinization of Lidocaine on the Pain of Skin Infiltration and Intravenous Catheterization. J. Clin Anesth, 5 November/December 1993, 456-456; Armel H. E. and Horowitz M., Alkalinization of Local Anesthesia with Sodium Bicarbonate-Preferred Method of Local Anesthesia. Urology. 1994. 43, 101; and Suraj Achar, M.D. and Suriti Kundu, M.D., Principles of Office Anesthesia: Part I. Infiltrative Anesthesia, *Am Fam Physician*. 2002 Jul. 1; 66(1):91-95.

A substantial drawback of buffering anesthetics is the substantial decreased shelf life of the resulting buffered anesthetics. Buffered anesthetics left on the shelf may not be effective after one week. Thus it has become common for professionals to undergo the time consuming process of buffering the anesthetic solution on site immediately prior to giving the injection. The medical professional will often attempt to mix about nine parts lidocaine solution (typically 1 to 2 percent) to about one part sodium bicarbonate solution (8.4 percent) in a syringe or anesthetic bottle just before the procedure. The 8.4% sodium bicarbonate solution is a commonly available strength which has 8.4 grams of sodium bicarbonate per one hundred total milliliters of liquid solution.

Syringes are commonly used, for example in the fields of medicine and dentistry, to deliver controlled quantities of fluids, typically liquids, to desired locations. One well-known type of hypodermic syringe is a carpule syringe 50 shown in FIGS. 4A-C and is specifically designed for dispensing fluid from a certain type of fluid container referred to in the art as a "carpule", such as those carpules 10 according to the present invention shown in FIGS. 1A-3B.

The conventional carpule syringe 50 and associated carpules further include U.S. Pat. No. 5,542,934 (multiple carpule syringe design); U.S. Pat. Nos. 5,330,440; 5,269,766; 5,112,307; 4,931,040; 4,919,657; 4,915,701; 4,490,142; 4,333,457; 3,848,593; and 2,671,450. These patents are incorporated herein by reference.

The conventional carpule syringe 50 includes the handle portion 52 which includes a finger grip and guard 54 and spring biased axially moveable piston engaging rod 56 as best shown in FIG. 4B. The conventional carpule syringe 50 further includes a tubular body or frame 58, sometimes called a barrel, that receives the carpule therein. The frame 58 is typically open on the side to receive a carpule therein, although rear loading carpule syringes 50 are also known. On a forward end of the frame 58 is a needle hub 60 that typically threadingly engages a needle. The conventional needle is attached to the hub 60 includes a rear piecing portion extending into the carpule through a sealed end thereof. The carpule syringe 50 will often include a removable needle guard 62 that can minimize accidental "sticking" incidents.

A carpule within the meaning of this invention is a hollow tubular device filled with medicament, or other material, to be dispensed through a needle attached to a carpule syringe, and wherein the carpule is configured to be received within the frame 58 of a carpule syringe 50, and has an axially movable plunger therein to be engaged and moved by with the rod 58 of the carpule syringe and a seal configured to be pierced by a rear piercing portion of the needle coupled to the needle hub 60.

There remains a need in the art to for a simple to operate, intuitive, accurate, cost effective apparatus and method for storing, transporting and in situ mixing of lidocaine and sodium bicarbonate and for delivery of buffered anesthetic solution.

SUMMARY OF THE INVENTION

Some of the above objects are achieved with syringe carpule for storing, transporting and in situ mixing of a local anesthetic, such as lidocaine, and buffer, such as sodium bicarbonate, and delivery of buffered anesthetic solution according to the present invention that comprises a hollow tubular body configured to be received within the frame of a carpule syringe, at least one axially movable plunger within the tubular body and configured to be engaged and moved by a rod of the carpule syringe, a seal configured to be pierced by a rear portion of a needle coupled to the carpule syringe, a first chamber defined within the hollow tubular body filled with anesthetic solution during storing and transport, a second chamber defined within the hollow tubular body filled with buffering solution during storing and transport; and a breachable separating member between the first chamber and the second chamber, wherein the separating member is configured to be removed for in situ mixing of the buffering solution and the anesthetic solution to allow for delivery of a buffered anesthetic solution.

These and other advantages of the present invention will be clarified in the brief description of the preferred embodiment taken together with the drawings in which like reference numerals represent like elements throughout.

BRIEF DESCRIPTION OF THE DRAWINGS

FIG. 1A is an exploded schematic sectional view of a carpule for storing, transporting and in situ mixing of a local anesthetic, such as lidocaine, and buffer, such as sodium bicarbonate, and delivery of buffered anesthetic solution from a carpule syringe in accordance with one embodiment of the present invention;

FIG. 1B is a sectional view of the carpule of FIG. 1A filled with local anesthetic, such as lidocaine, and buffer, such as sodium bicarbonate;

FIG. 2A is an exploded schematic sectional view of a carpule for storing, transporting and in situ mixing of a local anesthetic, such as lidocaine, and buffer, such as sodium bicarbonate, and delivery of buffered anesthetic solution from a carpule syringe in accordance with a second embodiment of the present invention;

FIG. 2B is a sectional view of the carpule of FIG. 2A filled with local anesthetic, such as lidocaine, and buffer, such as sodium bicarbonate;

FIG. 3A is an exploded schematic sectional view of a carpule for storing, transporting and in situ mixing of local anesthetic, such as lidocaine, and buffer, such as sodium bicarbonate, and delivery of buffered anesthetic solution from a carpule syringe in accordance with another embodiment of the present invention;

FIG. 3B is a sectional view of the carpule of FIG. 3A filled with local anesthetic, such as lidocaine, and buffer, such as sodium bicarbonate;

DESCRIPTION OF THE PREFERRED EMBODIMENTS

Figures 4A, 4B, 4C:
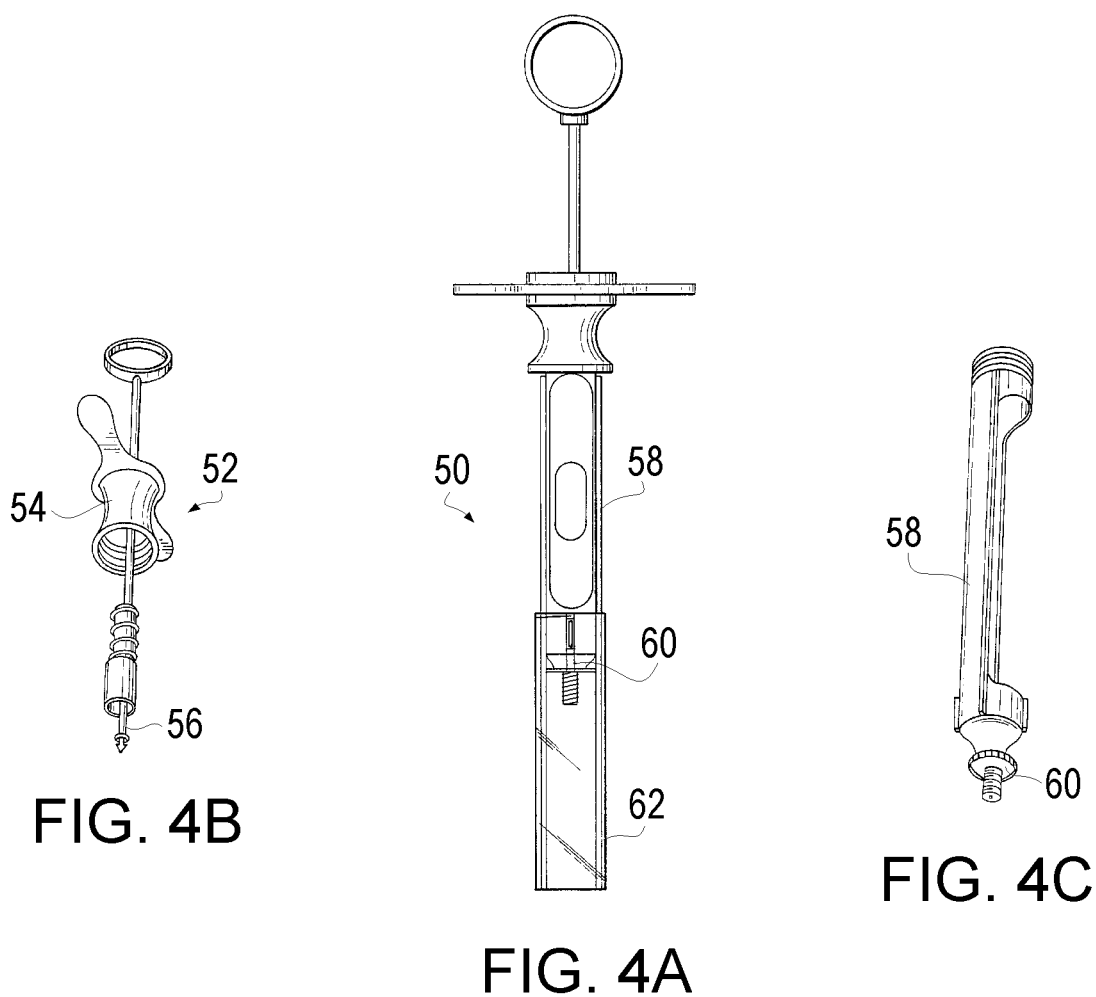
FIG. 4A is a perspective view a carpule syringe configured for use with the carpules of FIGS. 1-3.
FIG. 4B is a perspective view of the handle portion of the carpule syringe of FIG. 4A.
FIG. 4C is a perspective view of the frame portion of the carpule syringe of FIG. 4A.

FIG. 1A an exploded schematic sectional view of a carpule 10 for storing, transporting and in situ mixing of local anesthetic 16, such as lidocaine, and buffer 28, such as sodium bicarbonate, and delivery of buffered anesthetic solution from a carpule syringe 50 in accordance with one embodiment of the present invention, and FIG. 1B is a sectional view of the carpule 10 of FIG. 1A filled with local anesthetic 16, such as lidocaine, and buffer 28, such as sodium bicarbonate. It will be appreciated then that other local anesthetics 16 and buffers 28 may be implemented in the present invention other than lidocaine and sodium bicarbonate, however these being very common examples and thus particularly useful in implementing the invention, the disclosure will reference lidocaine 16 and sodium bicarbonate 28.

The syringe carpule 10 includes a hollow tubular body 12 configured to be received within the frame 58 of a carpule syringe 50. The body 12 is typically a cylindrical tube shape generally corresponding to the interior shape of the frame 58 and can be formed of conventional materials such as glass or plastics.

The syringe carpule 10 includes at least one axially movable plunger 32 which may have side seals 34. The plunger 32 is axially moveable within the tubular body 12 and configured to be engaged and moved by a rod 56 of the carpule syringe 50. The plunger 32 and seals 34 can be formed of conventional materials such as rubber or elastomeric polymers. The seals 34 engage the inner walls of the body 12 to prevent leakage and to advance fluid through the carpule 10 with advancement of the plunger 32 by rod 56.

The syringe carpule 10 includes at a seal 20 within cap 18, wherein the seal 20 configured to be pierced by a rear portion of a needle coupled to the needle hub 60 of the carpule syringe 50. The cap 18 is coupled to the body 12 such as crimped around a neck portion thereof as shown. The cap 18 may be formed of metal or polymeric material and the seal 20 is formed of a polymeric or other piercable material that can adequately seal the liquid within the body 12.

The syringe carpule 10 includes a first chamber 14 defined within the hollow tubular body 12 which is filled with anesthetic solution, namely lidocaine 16 during storing and transport. The lidocaine 16 will typically be a 1-4% lidocaine solution, generally a 1-2% lidocaine solution. The key aspect of the present invention is the provision of a second chamber 26 defined within the hollow tubular body 12 and filled with buffering solution 28 during storing and transport. The buffering solution 28 will typically be a sodium bicarbonate solution, generally containing 4-9% sodium bicarbonate. 4.2%, 5%, 7.5% and 8.4% represent commonly available sodium bicarbonate solutions for solution 28.

In the syringe carpule 10 of FIGS. 1A and B the body 12 includes a recess 22 receiving a second chamber body 24 therein. The second chamber body 24 may further include an annular ledge 30 configured to abut against an end of the body 12.

The second chamber body 24 further includes a breachable or frangible separating member 38 at the distal end thereof to be positioned between the first chamber 14 and the second chamber 26. The separating member 38 may in the form of a thin metal or plastic foil. Weakened "rupture" lines may be included in the member 38 to create defined breaking lines for the member 38.

In operation of the carpule 10 the separating member (or membrane) 38 is configured to be removed for in situ mixing of the buffering solution 28, namely sodium bicarbonate, and the anesthetic solution 16, namely lidocaine, to allow for delivery of a buffered anesthetic solution. In the embodiment shown in FIG. 1 the plunger 32 actually seals against the walls of the second chamber body 24 (which is considered part of the body 12) in transport and storage. Advancement of the plunger 32 will increase the pressure within the second chamber 26 causing the rupture of the separating member 38, possibly along weakened rupture or score lines therein for controlled breaking of the member 38. Mixing of the buffering solution 28, namely sodium bicarbonate, and the anesthetic solution 16 follows rupture of the membrane 38, and the user may agitate (shake) the carpule syringe 50 at this point to facilitate thorough mixing.

The invention contemplates the use of a special rod 56 including a needle piercing member thereon (not shown) that would piece the plunger 32 and extend through the length of the chamber 26 to mechanically pierce the member 38.

Following mixing, the buffered anesthetic solution can be dispensed in a conventional fashion through advancement of the plunger 32 along the body 12 via the rod 56. It is noted that the interior of the body 24 is the same shape and diameter as the inside of the chamber 14 so the plunger 32 maintains a similar sealing via seals 34 engagement along its travel. The member 38 is formed of a thin foil, membrane material that will not interfere with the sealing of the plunger 32.

FIG. 2A is an exploded schematic sectional view of a carpule 10 for storing, transporting and in situ mixing of lidocaine 16 and sodium bicarbonate 28 and delivery of buffered anesthetic solution from a carpule syringe 50 in accordance with a second embodiment of the present invention, and FIG. 2B is a sectional view of the carpule 10 of FIG. 2A filled with lidocaine 16 and sodium bicarbonate 28. The difference in the embodiment of FIGS. 2A and B from the embodiment of FIGS. 1A and B described above is that recess 22 for receipt of the body 24 forming the second chamber 26 is positioned at the front of the body 12. Additionally, body 12 and body 24 are shown including matching threads 36 for threading the body 24 into the recess 22 of the body 12 as shown in FIG. 2B. The membrane 38 between the chambers 14 and 26 is shown as a separate member. The cap 18 and seal 20 is attached, in this embodiment of FIGS. 2A and B, to the body 24.

The embodiment of FIGS. 2A and B can operate in the same manner as the embodiment of FIGS. 1A and B, wherein advancement of the plunger 32 increases pressure on the member 38 to rupture the member 38 to allow for mixing and forming the buffered anesthetic solution. Alternatively, the embodiment of FIGS. 2A and B also allows for the piecing end of the needle to pierce the membrane 38 in addition to piercing seal 20.

FIG. 3A is an exploded schematic sectional view of a carpule 10 for storing, transporting and in situ mixing of lidocaine 16 and sodium bicarbonate 28 and delivery of buffered anesthetic solution from a carpule syringe 50 in accordance with a third embodiment of the present invention, and FIG. 3B is a sectional view of the carpule 10 of FIG. 3A filled with lidocaine 16 and sodium bicarbonate 28. The embodiment of FIGS. 3A and B is similar to that of the embodiment of FIGS. 2A and B in that recess 22 for receipt of the body 24 forming the second chamber 26 is positioned at the front of the body 12. In this embodiment the chamber 24 is encapsulated within the cap 18 which is attached to a neck in the body 12, similar to the attachment of the embodiment of FIGS. 1A and B.

The embodiment of FIGS. 3A and B can also operate in the same manner as the embodiment of FIGS. 1A and B wherein advancement of the plunger 32 increases pressure on the member 38 to rupture the member 38 to allow for mixing and forming the buffered anesthetic solution. Alternatively, this embodiment, like the embodiment of FIGS. 2A and B, more conveniently allows for the piecing end of the needle attached to hub 60 of carpule syringe 50 to pierce the membrane 38 as well as piercing seal 20.

The scope of the invention is not to be limited by the illustrative examples described above. The scope of the present invention is defined by the appended claims and equivalents thereto.

What is claimed is:

1. A syringe carpule for storing, transporting, in situ mixing and delivery of buffered anesthetic solution, comprising:

A hollow tubular body configured to be received within the frame of a carpule syringe;

At least one axially movable plunger within the tubular body and configured to be engaged and moved by a rod of the carpule syringe;

A seal configured to be pierced by a rear portion of a needle coupled to the carpule syringe;

A first chamber defined within the hollow tubular body filled with one of an anesthetic solution or a buffering solution during storing and transport;

A second chamber defined within the hollow tubular body filled with the other of an anesthetic solution or a buffering solution during storing and transport, wherein the hollow tubular body includes a second chamber body and a recess receiving the second chamber body therein, wherein the second chamber body forms the second chamber and wherein the second chamber body further includes an annular ledge configured to abut against an end of the hollow tubular body; and A breachable separating member between the first chamber and the second chamber, wherein the separating member is configured to be breached for in situ mixing of the buffering solution and the anesthetic solution to allow for delivery of a buffered anesthetic solution.

2. The syringe carpule for storing, transporting, in situ mixing and delivery of buffered anesthetic solution according to claim 1 wherein the anesthetic solution includes 1-4% lidocaine.

3. The syringe carpule for storing, transporting, in situ mixing and delivery of buffered anesthetic solution according to claim 2 wherein the buffering solution includes sodium bicarbonate.

4. The syringe carpule for storing, transporting, in situ mixing and delivery of buffered anesthetic solution according to claim 2 wherein the buffering solution includes 4-9% sodium bicarbonate.

5. The syringe carpule for storing, transporting, in situ mixing and delivery of buffered anesthetic solution according to claim 1 wherein the plunger seals against the second chamber body in transport and storage.

6. The syringe carpule for storing, transporting, in situ mixing and delivery of buffered anesthetic solution according to claim 1 wherein the recess for receipt of the second chamber forming the second chamber is positioned at the rear of the hollow tubular body.

7. The syringe carpule for storing, transporting, in situ mixing and delivery of buffered anesthetic solution according to claim 1 wherein the recess for receipt of the second chamber body forming the second chamber is positioned at the front of the hollow tubular body.

8. A syringe carpule for storing, transporting, in situ mixing and delivery of buffered anesthetic solution, comprising:

A hollow tubular body configured to be received within the frame of a carpule syringe;

At least one axially movable plunger within the tubular body and configured to be engaged and moved by a rod of the carpule syringe;

A seal configured to be pierced by a rear portion of a needle coupled to the carpule syringe;

A first chamber defined within the hollow tubular body filled with one of an anesthetic solution or a buffering solution during storing and transport;

A second chamber defined within the hollow tubular body filled with the other of an anesthetic solution or a buffering solution during storing and transport, wherein the hollow tubular body includes a second chamber body and a recess receiving the second chamber body therein, wherein the second chamber body forms the second chamber; and A breachable separating member between the first chamber and the second chamber, wherein the separating member is configured to be breached for in situ mixing of the buffering solution and the anesthetic solution to allow for delivery of a buffered anesthetic solution, wherein the plunger seals against the second chamber body in transport and storage, and wherein an interior of the second chamber body is the same shape and diameter as the inside of the first chamber wherein the plunger is configured to travel along portions of both the first and second chamber and wherein the plunger maintains a similar sealing engagement along its travel.

9. A syringe carpule for storing, transporting, in situ mixing and delivery of buffered anesthetic solution, comprising:

A hollow tubular body configured to be received within the frame of a carpule syringe;

At least one axially movable plunger within the tubular body and configured to be engaged and moved by a rod of the carpule syringe;

A seal configured to be pierced by a rear portion of a needle coupled to the carpule syringe;

A first chamber defined within the hollow tubular body filled with one of an anesthetic solution or a buffering solution during storing and transport;

A second chamber defined within the hollow tubular body filled with the other of an anesthetic solution or a buffering solution during storing and transport, wherein the hollow tubular body includes a second chamber body and a recess receiving the second chamber body therein, wherein the second chamber body forms the second chamber; and A breachable separating member between the first chamber and the second chamber, wherein the separating member is configured to be breached for in situ mixing of the buffering solution and the anesthetic solution to allow for delivery of a buffered anesthetic solution, wherein the breachable separating member between the first chamber and the second chamber includes weakened rupture or score lines therein for controlled breaking of the member.

10. A syringe carpule for storing, transporting, in situ mixing and delivery of buffered anesthetic solution, comprising:

A hollow tubular body configured to be received within the frame of a carpule syringe;

At least one axially movable plunger within the tubular body and configured to be engaged and moved by a rod of the carpule syringe;

A seal configured to be pierced by a rear portion of a needle coupled to the carpule syringe;

A first chamber defined within the hollow tubular body filled with one of an anesthetic solution or a buffering solution during storing and transport;

A second chamber defined within the hollow tubular body filled with the other of an anesthetic solution or a buffering solution during storing and transport, wherein the hollow tubular body includes a second chamber body and a recess receiving the second chamber body therein, wherein the second chamber body forms the second chamber; and A breachable separating member between the first chamber and the second chamber, wherein the separating member is configured to be breached for in situ mixing of the buffering solution and the anesthetic solution to allow for delivery of a buffered anesthetic solution, wherein the hollow tubular body and second chamber body include matching threads for threading the second chamber body into the recess of the hollow tubular body.

11. A syringe carpule for storing, transporting, in situ mixing and delivery of buffered anesthetic solution, comprising:

A hollow tubular body configured to be received within the frame of a carpule syringe;

At least one axially movable plunger within the tubular body and configured to be engaged and moved by a rod of the carpule syringe;

A seal configured to be pierced by a rear portion of a needle coupled to the carpule syringe;

A first chamber defined within the hollow tubular body filled with one of an anesthetic solution or a buffering solution during storing and transport;

A second chamber defined within the hollow tubular body filled with the other of an anesthetic solution or a buffering solution during storing and transport, wherein the hollow tubular body includes a second chamber body and a recess receiving the second chamber body therein, wherein the second chamber body forms the second chamber; and A breachable separating member between the first chamber and the second chamber, wherein the separating member is configured to be breached for in situ mixing of the buffering solution and the anesthetic solution to allow for delivery of a buffered anesthetic solution, wherein the hollow tubular body includes a neck at a forward portion thereof, and further including cap coupled to the neck of the hollow tubular body, wherein the cap includes the seal configured to be pierced by a rear portion of a needle coupled to the carpule syringe.

12. The syringe carpule for storing, transporting, in situ mixing and delivery of buffered anesthetic solution according to claim 11 wherein the cap encapsulates the second chamber body.

13. The syringe carpule for storing, transporting, in situ mixing and delivery of buffered anesthetic solution according to claim 11 wherein both the cap seal and the breachable separating member are configured to be pierced by a rear portion of a needle coupled to a needle hub of the carpule syringe.

14. A syringe carpule for storing, transporting, in situ mixing and delivery of buffered lidocaine anesthetic solution, comprising A hollow tubular body configured to be received within the frame of a carpule syringe and including a neck at a forward portion thereof; At least one axially movable plunger within the tubular body and configured to be engaged and moved by a rod of the carpule syringe; A cap coupled to the neck of the hollow tubular body and including a seal configured to be pierced by a rear portion of a needle coupled to the carpule syringe; A first chamber defined within the hollow tubular body filled a lidocaine solution during storing and transport; A second chamber defined within the hollow tubular body filled with the a buffering solution during storing and transport; and A breachable separating member between the first chamber and the second chamber, wherein the separating member is configured to be breached for in situ mixing of the buffering solution and the lidocaine solution to allow for delivery of a buffered anesthetic solution, wherein the lidocaine solution includes 1-4% lidocaine and the buffering solution includes sodium bicarbonate with 4-9% sodium bicarbonate, wherein the hollow tubular body includes a second chamber body and a recess receiving the second chamber body therein, wherein the second chamber body forms the second chamber, and wherein the second chamber body further includes an annular ledge configured to abut against an end of the hollow tubular body.

15. The syringe carpule for storing, transporting, in situ mixing and delivery of buffered anesthetic solution according to claim 14 wherein both the cap seal and the breachable separating member are configured to be pierced by a rear portion of a needle coupled to a needle hub of the carpule syringe.

\* \* \* \* \*